United States Patent
Nitin et al.

(10) Patent No.: US 12,243,539 B2
(45) Date of Patent: Mar. 4, 2025

(54) SURGICAL MICROSCOPE SYSTEM AND CORRESPONDING SYSTEM, METHOD AND COMPUTER PROGRAM FOR A SURGICAL MICROSCOPE SYSTEM

(71) Applicant: Leica Instruments (Singapore) Pte. Ltd., Singapore (SG)

(72) Inventors: Roy Nitin, Bangalore (IN); Manoj Jangra, Bangalore (IN)

(73) Assignee: Leica Instruments (Singapore) Pte Ltd., Singapore (SG)

( * ) Notice: Subject to any disclaimer, the term of this patent is extended or adjusted under 35 U.S.C. 154(b) by 338 days.

(21) Appl. No.: 17/656,261

(22) Filed: Mar. 24, 2022

(65) Prior Publication Data

US 2022/0310099 A1    Sep. 29, 2022

(30) Foreign Application Priority Data

Mar. 24, 2021    (DE) .......................... 102021107420.7

(51) Int. Cl.
     *G10L 15/22*      (2006.01)
     *A61B 90/20*      (2016.01)
     (Continued)

(52) U.S. Cl.
     CPC .............. *G10L 17/22* (2013.01); *A61B 90/20* (2016.02); *G02B 21/0012* (2013.01);
     (Continued)

(58) Field of Classification Search
     CPC ....... G10L 15/22; G10L 15/06; G10L 15/063; G10L 15/065; G10L 15/07; G10L 15/10;
     (Continued)

(56) References Cited

U.S. PATENT DOCUMENTS

| 4,989,253 | A | 1/1991 | Liang et al. |
| 7,286,992 | B2 | 10/2007 | Sander et al. |

(Continued)

FOREIGN PATENT DOCUMENTS

| CN | 112149606 A | 12/2020 |
| EP | 3632365 A1 | 4/2020 |
| EP | 3744285 A1 | 12/2020 |

OTHER PUBLICATIONS

Synaptive Medical, Modus V, https://www.synaptivemedical.com/products/modus-v (archived at https://web.archive.org/web/20210304192348/https://www.synaptivemedical.com/products/modus-v/ on Mar. 4, 2021).

*Primary Examiner* — Qi Han
(74) *Attorney, Agent, or Firm* — 2SPL Patent Attorneys PartG mbB; Kieran O'Leary

(57) ABSTRACT

Examples relate to a surgical microscope system and to a corresponding system, method and computer program for a surgical microscope system. The system comprises one or more processors and one or more storage devices. The system is configured to obtain an audio signal from a microphone of the surgical microscope system. The system is configured to analyze the audio signal locally to detect one or more spoken commands within the audio signal. A user-specific voice profile is used to determine whether the one or more spoken commands are uttered by a user associated with the user-specific voice profile. The system is configured to control the surgical microscope system based on the detected one or more spoken commands if the one or more spoken commands are uttered by the user associated with the user-specific voice profile.

15 Claims, 2 Drawing Sheets

(51) Int. Cl.
*G02B 21/00* (2006.01)
*G10L 17/06* (2013.01)
*G10L 17/22* (2013.01)
*H04R 1/02* (2006.01)
*H04R 1/08* (2006.01)

(52) U.S. Cl.
CPC .............. *G10L 17/06* (2013.01); *H04R 1/028* (2013.01); *H04R 1/08* (2013.01)

(58) Field of Classification Search
CPC ....... G10L 15/183; G10L 15/20; G10L 15/26; G10L 2015/0631–0638; G10L 2015/221–228; G10L 17/06; G10L 17/00; G10L 17/02; G10L 17/08; G10L 17/22; G10L 17/26
USPC .... 704/275, 270.1, 270, 277, 243, 246, 250, 704/251, 255
See application file for complete search history.

(56) References Cited

U.S. PATENT DOCUMENTS

| | | | |
|---|---|---|---|
| 10,013,983 B1* | 7/2018 | Johnson | G06V 40/16 |
| 2007/0150278 A1* | 6/2007 | Bates | G10L 15/197 |
| | | | 704/E15.023 |
| 2014/0039893 A1 | 2/2014 | Weiner | |
| 2018/0315429 A1* | 11/2018 | Taple | G10L 17/24 |
| 2020/0297202 A1 | 9/2020 | Tashiro et al. | |
| 2021/0250641 A1* | 8/2021 | Aguiar | H04N 21/4223 |
| 2022/0249178 A1* | 8/2022 | Charles | A61B 17/00 |

\* cited by examiner

SURGICAL MICROSCOPE SYSTEM AND CORRESPONDING SYSTEM, METHOD AND COMPUTER PROGRAM FOR A SURGICAL MICROSCOPE SYSTEM

TECHNICAL FIELD

Examples relate to a surgical microscope system and to a corresponding system, method and computer program for a surgical microscope system.

BACKGROUND

The usage and control of medical devices, such as surgical microscope systems, is a field of research and development. In general terms, surgical microscope systems are systems that are built around a microscope that is used in a surgical setting, i.e., during surgery. During surgery, for example during neuro-surgery, the surgeon may desire not to take their eyes of the surgical site, and thus off the oculars or display of the microscope.

Speech recognition technology may be used for operating a device without having to touch the device. However, such speech recognition technology is often powered by complex neural networks, which are employed on a server that is accessible via the internet, and which provides a user-agnostic speech recognition service.

SUMMARY

Various embodiments of the present disclosure are based on the finding, that a voice-based interface may be used to control the microscope. However, speech recognition technology that is only accessible via the internet may be unsuitable for the specific challenges of the use of speech recognition in surgical microscope systems. For example, many surgical microscope systems lack access to the internet, e.g., for safety reasons, or as wireless communication is prohibited in the operating room and an ethernet connection might not be available. Furthermore, in surgical microscope systems, it may be paramount that the commands being executed by the surgical microscope system are uttered by the person in charge, e.g., the surgeon, and are not based on a misinterpretation of a comment uttered by a bystander, such as surgical personnel.

Various examples of the present disclosure relate to a system for a surgical microscope system. The system comprises one or more processors and one or more storage devices. The system is configured to obtain an audio signal from a microphone of the surgical microscope system. The system is configured to analyze the audio signal locally to detect one or more spoken commands within the audio signal. A user-specific voice profile is used to determine whether the one or more spoken commands are uttered by a user associated with the user-specific voice profile. The system is configured to control the surgical microscope system based on the detected one or more spoken commands if the one or more spoken commands are uttered by the user associated with the user-specific voice profile. By using speech recognition, the surgical microscope system may be controlled without touching the surgical microscope systems, and without taking the eyes off the patient. By employing a user-specific voice profile, the system can ascertain that the commands are uttered by a user that is authorized to trigger the respective commands.

For example, the system may be configured to discard spoken commands of users other than the user associated with the user-specific voice profile. Consequently, other surgical personnel may exchange information in the operating room without triggering a command at the surgical microscope system.

In general, a decision on whether a spoken command is implemented is a binary decision—the command is either performed, or it is not performed. Underlying this decision, a more granular determination may be made, with respect to the recognition of the person having uttered the command, and also with respect to whether the command having been detected matches the spoken command. For example, the system may be configured to determine a confidence level for the detection of the one or more spoken commands. The confidence level may indicate a likelihood for the one or more spoken commands being recognized correctly and for the one or more spoken commands being uttered by the user associated with the user-specific voice profile. The surgical microscope system may be controlled if the confidence level is sufficiently high. In other words, the surgical microscope system might only be discarded if the confidence level is high for both conditions.

In various examples, the user-specific voice profile is specific to a surgeon actively using the surgical microscope system and/or to a surgeon that is in command of the surgical microscope system. Consequently, control of the surgical microscope system via speech recognition may be limited to the surgeon actively using the surgical microscope system and/or to the surgeon being in charge of the surgical procedure.

To initiate the system, the user-specific voice profile may be loaded into the system. This may be done by signing the user into the system. For example, the surgeon may sign into the system, e.g., by swiping a badge, by select their profile from a list, or by entering a username and password. The system may be configured to load the user-specific voice profile from the one or more storage devices based on the sign-in of the user at the surgical microscope system.

In some examples, a single user-specific voice profile is loaded for a single user of the surgical microscope system. In this case, the voice uttering the spoken command might only be compared with the user-specific voice profile of the single user.

In some examples, however, multiple users are supported. For example, two or more user-specific voice profiles may be used to determine whether the one or more spoken commands are uttered by a user of two or more users associated with two or more user-specific voice profiles. Each user may be associated with one of the voice profiles. The system may be configured to identify the user of the two or more users using the voice profile associated with the user. The system may be configured to control the surgical microscope system based on the detected one or more spoken commands if the user that has uttered the one or more spoken commands is a surgeon actively using the surgical microscope system. This way, the user-specific voice profiles need not be explicitly loaded, and the voice uttering the spoken command can be compared to any of the loaded user-specific voice profiles. However, the surgeon actively using the surgical microscope system may sign into the surgical microscope system, and mark themselves as being the surgeon actively using the surgical microscope system.

The user-specific voice profile may be based on at least one of a wavelength range of the voice of the user and a vocal amplitude of the user. Both the wavelength range and the vocal amplitude may be used to distinguish different users.

In general, the system may be configured to analyze the audio signal locally to detect one or more keywords or key phrases, and to detect the one or more spoken commands based on an association between the one or more keywords or key phrases and the one or more spoken commands. By using pre-defined keywords or key phrases, ambiguities may be reduced.

In various examples, the system is configured to detect the one or more spoken commands within the audio signal without involving an external entity. In other words, the speech recognition is performed locally, on device, in the system.

In various examples, the system is configured to analyze the audio signal using the user-specific voice profile, using a language model, and using a dictionary of keywords or key phrases. For example, the user-specific voice profile may be used to ascertain that the command is uttered by an authorized user. The language model may be used to extract words from the recorded audio. The dictionary or keywords or key phrases may be used to identify valid commands.

For example, the dictionary of keywords or key phrases may comprise keywords or key phrases that are associated with a plurality of commands available at the microscope system. The system may comprise a mapping between the keywords or key phrases and the plurality of commands. The system may be configured to control the surgical microscope system based on the mapping between the keywords or key phrases and the plurality of commands. As mentioned above, the keywords and key phrases, and their explicit mapping to the respective commands, may be used to reduce ambiguities.

There are various aspects of the surgical microscope system that may be controlled via the proposed concept. For example, the system may be configured to control at least one of an illumination of the surgical microscope system, an imaging mode of a microscope of the surgical microscope system, a zoom functionality of the microscope, a focusing functionality of the microscope, an auto-focusing functionality of the microscope, a robotic arm of the surgical microscope system, a video recording functionality of the surgical microscope system, and a still image recording functionality of the surgical microscope system.

Various aspects of the present disclosure relate to a surgical microscope system comprising the system presented above, a microscope, and a microphone.

Various aspects of the present disclosure relate to a method for a surgical microscope system. The method comprises obtaining an audio signal from a microphone of the surgical microscope system. The method comprises analyzing the audio signal locally to detect one or more spoken commands within the audio signal. A user-specific voice profile is used to determine whether the one or more spoken commands are uttered by a user associated with the user-specific voice profile. The method comprises controlling the surgical microscope system based on the detected one or more spoken commands if the one or more spoken commands are uttered by the user associated with the user-specific voice profile.

Various aspects of the present disclosure relate to a computer program with a program code for performing the above method when the computer program is executed on a processor.

SHORT DESCRIPTION OF THE FIGURES

Some examples of apparatuses and/or methods will be described in the following by way of example only, and with reference to the accompanying figures, in which.

DETAILED DESCRIPTION

Various examples will now be described more fully with reference to the accompanying drawings in which some examples are illustrated. In the figures, the thicknesses of lines, layers and/or regions may be exaggerated for clarity.

Figure 1A:
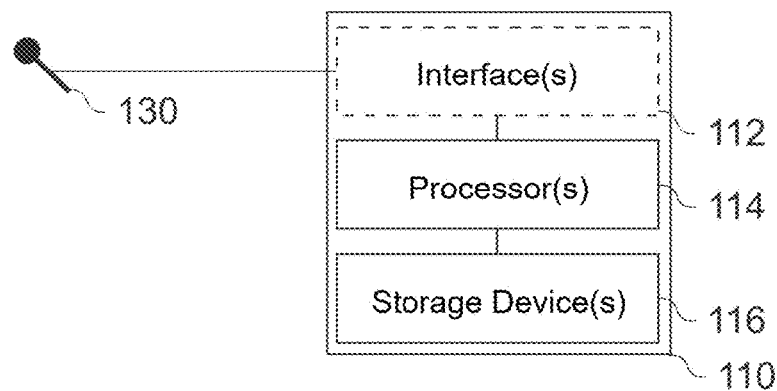
FIG. 1a shows a block diagram of an example of a system for a surgical microscope system.
Figure 1B:
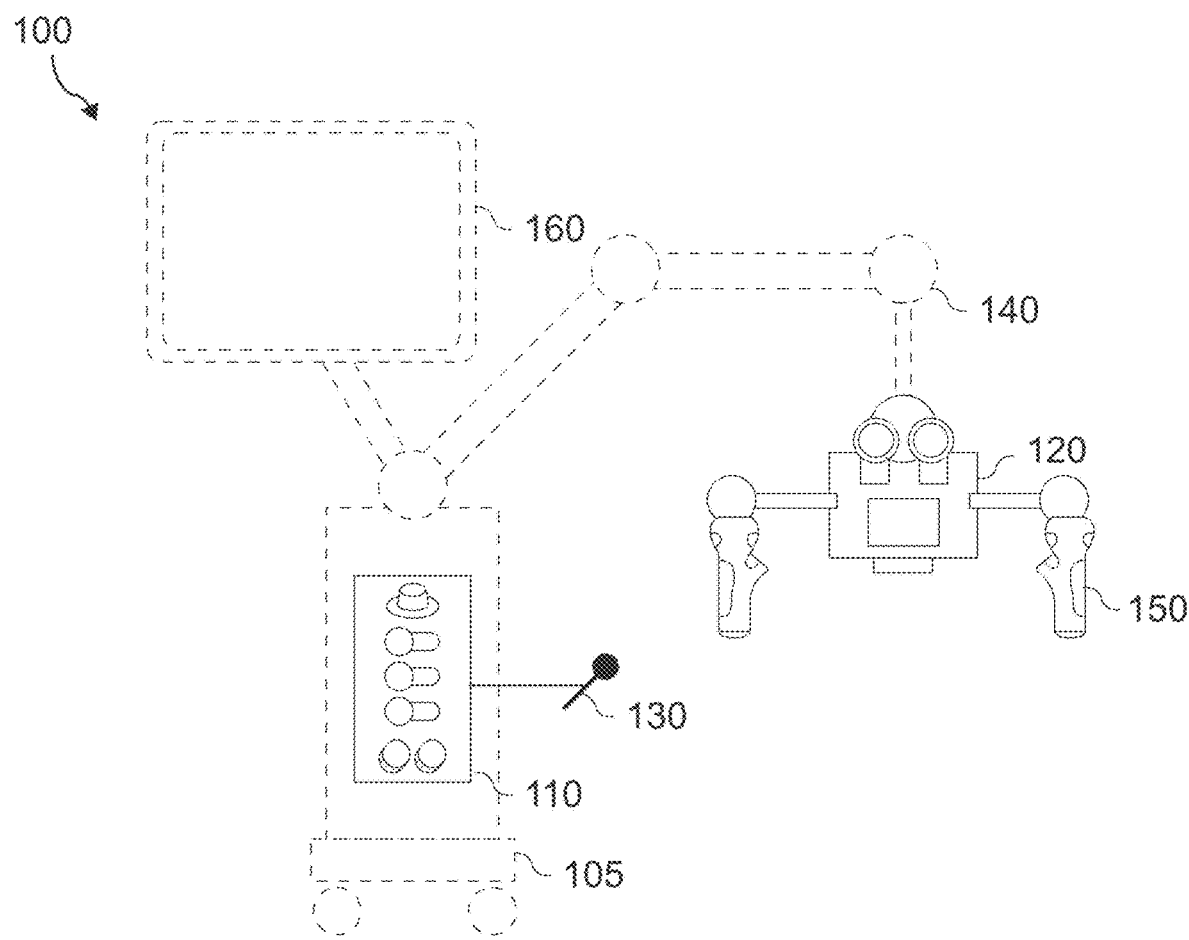
FIG. 1b shows a schematic diagram of an example of a surgical microscope system.

FIG. 1a shows a block diagram of an example of a system 110 for a surgical microscope system 100 (as shown in FIG. 1b). The system 110 comprises one or more processors 114 and one or more storage devices 116. Optionally, the system further comprises one or more interfaces 112. The one or more processors 114 are coupled to the one or more storage devices 116 and to the optional one or more interfaces 112. In general, the functionality of the system is provided by the one or more processors, in conjunction with the one or more interfaces (for exchanging information, e.g., for providing a control signal or for obtaining an audio signal) and/or with the one or more storage devices (for storing and/or retrieving information).

The system is configured to obtain (e.g., receive) an audio signal from a microphone 130 of the surgical microscope system. The system is configured to analyze the audio signal locally to detect one or more spoken commands within the audio signal. A user-specific voice profile is used to determine whether the one or more spoken commands are uttered by a user associated with the user-specific voice profile. The system is configured to control the surgical microscope system based on the detected one or more spoken commands if the one or more spoken commands are uttered by the user associated with the user-specific voice profile.

Embodiments of the present disclosure relate to a system, method, and computer program for a surgical microscope system. In general, a microscope is an optical instrument that is suitable for examining objects that are too small to be examined by the human eye (alone). For example, a microscope may provide an optical magnification of a sample. In modern microscopes, the optical magnification is often provided for a camera or an imaging sensor, such as an optical imaging sensor of the microscope 120 that is shown in FIG. 1b. The microscope 120 may further comprise one or more optical magnification components that are used to magnify a view on the sample, such as an objective (i.e., lens).

There are a variety of different types of microscopes. If the microscope is used in the medical or biological fields, the object being viewed through the microscope may be a sample of organic tissue, e.g., arranged within a petri dish or present in a part of a body of a patient. In the context of the present disclosure, the microscope 120 is part of a (neuro) surgical microscope system 100, e.g., a microscope to be used during a (neuro)surgical procedure. Such a system is shown in FIG. 1b, for example. Accordingly, an object being viewed through the microscope may be a sample of organic tissue of a patient. Although embodiments are described in connection with a microscope, they may also be applied, in a more general manner, to any optical device, and to any medical device.

The above system 110 is suitable for use with a surgical microscope system, e.g., as part the surgical microscope system 100 shown in FIG. 1b. FIG. 1b shows a schematic diagram of an example of a surgical microscope system 100 comprising the system 110, the microscope 120 and a microphone 130. The microscope system shown in FIG. 1b is a surgical microscope system. However, the system 110 may be used with other microscope systems, optical systems and medical devices as well. The surgical microscope system 100 shown in FIG. 1b comprises a number of optional components, such as a base unit 105 (comprising the system 110) with a (rolling) stand, a (robotic or manual) arm 140 which holds the microscope 120 in place, and which is coupled to the base unit 105 and to the microscope 120, steering handles 150 that are attached to the microscope 120, and a display 160. In the context of this application, the term "surgical microscope system" is used, in order to cover the portions of the system that are not part of the actual microscope (which comprises the optical components), but which are used in conjunction with the microscope, such as the display or an illumination system.

The system is configured to obtain the audio signal from the microphone 130 of the surgical microscope system. For example, the audio signal may be received an analog signal by the system (e.g., via the one or more interfaces 112), and digitized by the system. Alternatively, the audio signal may be received as a digital signal. In this case, the audio signal may be digitized by the microphone or by a separate analog-to-digital converter. For example, the microphone may be a microphone of a headset being worn by the surgeon, or the microphone may be arranged at the microscope, e.g., in close proximity to the surgeon actively using the surgical microscope system.

The system is configured to analyze the audio signal locally to detect one or more spoken commands within the audio signal. In this context, "analyzed locally" means, that the audio signal is analyzed by the system itself, e.g., without involving an external entity, such as a server that is accessible via the internet. For example, the system may be configured to detect the one or more spoken commands within the audio signal without involving an external entity, such as a server. For example, the analysis of the audio signal may be performed by the one or more processors 114 of the system. For example, a speech recognition framework or application programming interface (API) may be used to analyze the audio signal.

In general, the speech recognition or voice control system used in the proposed concept is application-specific, i.e., it is being used to control a specific entity. In this context, advanced functionalities, such as natural language processing, might not be suitable. Instead, fixed keywords and key phrases may be used. For example, the system may be configured to analyze the audio signal locally to detect one or more keywords or key phrases. For example, the keywords or key phrases may be defined in a dictionary of keywords or key phrases. Accordingly, the system may be configured to analyze the audio signal using a dictionary of keywords or key phrases. For example, the keywords or key phrases may be pre-defined and thus immutable or fixed. Alternatively, each user may define user-defined keywords or key phrases, or define synonyms to the pre-defined keywords or key phrases. The system may be configured to detect the one or more spoken commands based on an association between the one or more keywords or key phrases and the one or more spoken commands. In other words, when the system detects a keyword or key phrase that is associated with a spoken command, the respective spoken command may be detected.

Before the audio signal is analyzed with respect to keywords or key phrases, a language model may be used to detect individual words and/or combination of words in the audio signal. For example, the language model may be specific to the language being used for the keyword and key phrases. For example, the system may be configured to extract a sequence of words from the audio signal using the language model. In this sequence of words, the keywords or key phrases may be detected. In other words, the system may be configured to detect the one or more keywords or key phrases, e.g., using a dictionary of keywords or key phrases, in the sequence of words, with the sequence of words being extracted based on the language model. Accordingly, the system may be configured to analyze the audio signal using a language model and using a dictionary of keywords or key phrases.

A third component of the analysis of the audio signal is the user-specific voice profile. For example, the system may be configured to analyze the audio signal using the user-specific voice profile, using a language model, and using a dictionary of keywords or key phrases. The user-specific voice profile is used to determine whether the one or more spoken commands are uttered by a user associated with the user-specific voice profile. In other words, the user-specific voice profile is used to avoid the system mistakenly controlling the surgical microscope system based on an utterance of a person not being authorized to control the surgical microscope system. In general, the person or persons being authorized to control the surgical microscope system is the surgeon, e.g., a surgeon that is currently using the microscope, or a surgeon that is in command of the surgical microscope system (e.g., a supervising surgeon). Accordingly, the user-specific voice profile may be specific to a surgeon actively using the surgical microscope system and/or to a surgeon that is in command of the surgical microscope system.

In general, the user-specific voice profile may define at least one of the two following parameters: an altitude of the voice (expressed as a wavelength band) and an amplitude of the voice (e.g., a volume or volume profile) of the user. In other words, the user-specific voice profile may be based on at least one of a wavelength range of the voice of the user and a vocal amplitude of the user. For example, the system may be configured to determine the wavelength range of a voice contained in the audio signal, and to compare the wavelength range of the voice contained in the audio signal to the wavelength range of the voice of the user stored in the user-specific voice profile. Additionally or alternatively, the system may be configured to determine the vocal amplitude of the voice contained in the audio signal, and to compare the vocal amplitude of the voice contained in the audio signal to the vocal amplitude stored in the user-specific voice profile. If the wavelength ranges match or differ by at most a first threshold value, and/or if the vocal amplitudes match or differ by at most a second threshold value, the one or more spoken commands may be deemed to be uttered by the user associated with the user-specific voice profile.

As mentioned above, the properties of the voice contained in the audio signal may be compared to the user-specific voice profile. Based on the comparison, a confidence level regarding the one or more spoken commands being uttered by the user associated with the user-specific voice profile may be determined (by the system). For example, the better the match between the wavelength ranges and the vocal amplitudes, the higher the confidence level regarding the one or more spoken commands being uttered by the user associated with the user-specific voice profile may be. For example, the confidence level regarding the one or more spoken commands being uttered by the user associated with the user-specific voice profile may indicate a likelihood for the one or more spoken commands uttered by the user associated with the user-specific voice profile.

In addition, a confidence level regarding the one or more spoken commands being recognized correctly may be determined (by the system). For example, during the extraction of the words from the audio signal, the language model may provide a confidence level for the respective words being recognized correctly, which may be used to determine the confidence level regarding the one or more spoken commands being recognized correctly (as the spoken commands are derived from the keywords or key phrases, which are detected based on the extraction of the words). For example, the confidence level regarding the one or more spoken commands being recognized correctly may indicate a likelihood for the one or more spoken commands being recognized correctly.

Together, a common confidence level for the detection of the one or more spoken commands may be determined, which may be used to decide on whether the command is being issued. For example, the system may be configured to determine the confidence level for the detection of the one or more spoken commands, e.g., based on the confidence level regarding the one or more spoken commands being uttered by the user and based on the confidence level for the respective words being recognized correctly. The confidence level for the detection of the one or more spoken commands may indicate a likelihood for the one or more spoken commands being recognized correctly and for the one or more spoken commands being uttered by the user associated with the user-specific voice profile.

In general, the system may use one of two approaches with respect to the user-specific voice profiles. For example, a single user-specific voice profile may be loaded at a time, of the user that is actively using the surgical microscope system. In other words, a single user-specific voice profile may be loaded for a single user of the surgical microscope system. Alternatively, multiple user-specific voice profiles may be loaded at the same time (e.g., of all surgeons working in a department of a hospital), but the system may control the surgical microscope system only if the one or more spoken commands are uttered by one or more users that are marked as actively using or being in control of the surgical microscope system, e.g., by a single surgeon, or by a team of surgeons sharing control over the surgical microscope system. In this case, two or more user-specific voice profiles may be used to determine whether the one or more spoken commands are uttered by a user of two or more users associated with two or more user-specific voice profiles. Each of the users may be associated with one of the voice profiles. The system may be configured to identify the user of the two or more users using the voice profile associated with the user. In effect, if the user being identified is a surgeon, e.g., a single surgeon or a surgeon of a team of surgeons sharing control over the surgical microscope system, the surgical microscope system may be controlled based on the one or more spoken commands.

In both cases, the user or users (surgeon or surgeons) may sign into the surgical microscope system, to load their user-specific voice profile (in the former case), or to mark themselves as being the surgeon actively using the surgical microscope system (in the latter case). In other words, the system may be configured to load the user-specific voice profile from the one or more storage devices based on a sign-in of the user at the surgical microscope system, or the system may be configured to mark the user associated with a user-specific voice profile as actively using the surgical microscope system based on the sign-in of the user at the surgical microscope system.

The system is configured to control the surgical microscope system based on the detected one or more spoken commands if the one or more spoken commands are uttered by the user associated with the user-specific voice profile. For example, the system may be configured to control the surgical microscope system based on the detected one or more spoken commands if the voice contained in the audio signal, i.e., the voice uttering the one or more commands, matches the user-specific voice profile with respect to wavelength range and/or vocal amplitude (with a wavelength range or vocal amplitude being within a threshold around the respective values of the user-specific voice profile counting as match). To make a mode fine-grained determination, the confidence level regarding the one or more spoken commands being uttered by the user associated with the user-specific voice profile may be used. For example, the system may be configured to control the surgical microscope system based on the one or more spoken commands if the confidence level regarding the one or more spoken commands being uttered by the user associated with the user-specific voice profile is above a threshold.

In addition, the confidence level for the respective words being recognized correctly may be used to decide on whether the surgical microscope system is to be controlled. In other words, in addition to the one or more spoken commands being uttered by the "right" user, another condition may be that the respective words of the one or more spoken commands have been properly recognized. For example, the system may be configured to control the surgical microscope system based on the one or more spoken commands if the confidence level for the respective words being recognized correctly is above a threshold. For example, the surgical microscope system may be controlled if the confidence level for the detection of the one or more spoken commands, which may include the confidence levels introduced above, is sufficiently high, e.g. above threshold for the confidence level for the detection of the one or more spoken commands.

If the system determines that the one or more spoken commands were uttered by another user, e.g., a user that does not have authorization to control the surgical microscope system, the one or more spoken commands may be discarded. In other words, the system is configured to discard spoken commands of users other than the user associated with the user-specific voice profile. In case two or more user-specific voice profiles are loaded, the surgical microscope system may be controlled if the user being identified is authorized to control the surgical microscope system. For example, this is the case if the user being identified is the surgeon actively using the surgical microscope system or the surgeon being in (shared) control of the surgical microscope system. For example, the system may be configured to control the surgical microscope system based on the detected one or more spoken commands if the user that has uttered the one or more spoken commands (as identified by the system) is a surgeon actively using the surgical microscope system or a surgeon being in (shared) control of the surgical microscope system. If not, i.e., if the user that has been identified is deemed not to be actively using the surgical microscope system or deemed not to be in (shared) control of the surgical microscope system, the one or more spoken commands may be discarded as well. The same holds true if the confidence level for the detection of the one or more spoken commands, the confidence level for the respective words being recognized correctly or the confidence level regarding the one or more spoken commands being uttered by the user associated with the user-specific voice profile is below the respective threshold.

To translate the spoken commands into control instructions being transmitted to the respective components of the surgical microscope system, a mapping between the keywords or key phrases and the actual commands (i.e., control instructions or control signals) being issued may be used. For example, the dictionary of keywords or key phrases may comprise keywords or key phrases that are associated with a plurality of commands available at the microscope system. A mapping between the keywords or key phrases of the dictionary and the plurality of commands available at the microscope system may be used to translate the detected keywords into the commands being used to control the surgical microscope system. In other words, the system may comprise a mapping between the keywords or key phrases and the plurality of commands. For example, the mapping may be stored in the one or more storage devices. Consequently, system may be configured to determine the command or commands associated with the keywords or key phrases, and to control the surgical microscope system based on the determined command or commands. In effect, the system may be configured to control the surgical microscope system based on the mapping between the keywords or key phrases and the plurality of commands. For example, the system may be configured to control the surgical microscope system based on the command or commands being associated with the keyword(s) or key phrase(s) detected within the audio signal, as part of the one or more spoken commands.

There are a variety of different functionalities of the surgical microscope system that can be controlled via voice control. For example, any functionality that is commonly accessible via a handle button/control stick or foot pedal may be controlled via the voice control system. For example, the system may be configured to control an illumination of the surgical microscope system, e.g., an intensity of the illumination, or a wavelength spectrum of the illumination. For example, the system may be configured to control an imaging mode of a microscope of the surgical microscope system, e.g., to switch between a reflectance imaging mode and one or more fluorescence imaging modes. For example, the system may be configured to control a zoom functionality of the microscope, e.g., to increase or decrease a zoom level. For example, the system may be configured to control a focusing functionality of the microscope and/pr an auto-focusing functionality of the microscope, e.g., to move the focus, or to enable or disable the autofocus functionality. For example, the system may be configured to control the robotic arm 140 of the surgical microscope system, e.g., to increase or decrease a working distance. For example, the system may be configured to control a video recording functionality of the surgical microscope system, e.g., to start or stop a recording. For example, the system may be configured to control a still image recording functionality of the surgical microscope system, e.g., to trigger a capture of the image being shown in the oculars of the microscope. Additionally or alternatively, the system may be configured to control, based on the detected one or more spoken commands and if the one or more spoken commands are uttered by the user associated with the user-specific voice profile, one or more external devices being coupled with the surgical microscope system, such as an endoscope or an image-guided surgery (IGS) system.

The one or more interfaces 112 may correspond to one or more inputs and/or outputs for receiving and/or transmitting information, which may be in digital (bit) values according to a specified code, within a module, between modules or between modules of different entities. For example, the one or more interfaces 112 may comprise interface circuitry configured to receive and/or transmit information. In embodiments the one or more processors 114 may be implemented using one or more processing units, one or more processing devices, any means for processing, such as a processor, a computer or a programmable hardware component being operable with accordingly adapted software. In other words, the described function of the one or more processors 114 may as well be implemented in software, which is then executed on one or more programmable hardware components. Such hardware components may comprise a general-purpose processor, a Digital Signal Processor (DSP), a micro-controller, etc. In at least some embodiments, the one or more storage devices 116 may comprise at least one element of the group of a computer readable storage medium, such as a magnetic or optical storage medium, e.g., a hard disk drive, a flash memory, Floppy-Disk, Random Access Memory (RAM), Programmable Read Only Memory (PROM), Erasable Programmable Read Only Memory (EPROM), an Electronically Erasable Programmable Read Only Memory (EEPROM), or a network storage.

More details and aspects of the system and surgical microscope system are mentioned in connection with the proposed concept or one or more examples described above or below (e.g., FIGS. 2 to 4). The system and surgical microscope system may comprise one or more additional optional features corresponding to one or more aspects of the proposed concept or one or more examples described above or below.

Figure 2:
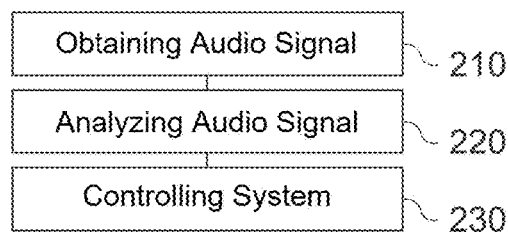
FIG. 2 shows a flow chart of an example of a method for a surgical microscope system.

FIG. 2 shows a flow chart of an example of a corresponding method for a surgical microscope system, e.g., for the surgical microscope system 100 of FIG. 1b. For example, the method may be performed by the system 110 introduced in connection with FIGS. 1a and/or 1b. The method comprises obtaining 210 an audio signal from a microphone 130 of the surgical microscope system. The method comprises analyzing 220 the audio signal locally to detect one or more spoken commands within the audio signal. A user-specific voice profile is used to determine whether the one or more spoken commands are uttered by a user associated with the user-specific voice profile. The method comprises controlling 230 the surgical microscope system based on the detected one or more spoken commands if the one or more spoken commands are uttered by the user associated with the user-specific voice profile.

Optionally, the method may comprise one or more further features, e.g., one or more features introduced with the system or surgical microscope system introduced in connection with FIGS. 1a and/or 1b.

More details and aspects of the method are mentioned in connection with the proposed concept or one or more examples described above or below (e.g., FIGS. 1a to 1b, 3 to 4). The method may comprise one or more additional optional features corresponding to one or more aspects of the proposed concept or one or more examples described above or below.

Various aspects of the present disclosure relate to a method for controlling a microscope using a voice profile loaded at the runtime specific to user. In other words, the proposed concept relates to a voice-controlled microscope, and is related to the voice recognition and the related software applications which can be used to control a microscope or surgical device. In particular, the proposed concept relates to an offline speech recognition system/framework which can be used to selectively load the voice profile of a user out of many voice profiles existing in the system and interact with the instrument based on the loaded voice profile.

While operating the microscope, without the use of a speech-recognition system, surgeons often put down the tools, use for example the CAN Handles and Joystick to adjust the settings, pick the tools again and proceed forward. The whole cycle may be repeated numerous times during an operation and can be detrimental to the workflow of the surgeon. In some examples of the present concept, the functionality of the CAN handles, e.g., the entire functionality or parts of the functionality, may be replaced by voice control, which may improve the usability of the microscope.

While there are voice-controlled systems in use for controlling medical devices, such voice-controlled systems often require an active internet connection for the speech recognition to be carried out on the "cloud" or "remote online server". Very few or none work in offline mode. The "Online" versions of the systems often work regardless of the voice uttering the command, which may be problematic in the medical world, where there are group of specialized people working towards a common operation, but the voice commands should be recognized only based on the active loaded voice profile and not just any spoken command.

In various examples of the present disclosure, first, an available voice profile (e.g. a user-specific voice profile) of the surgeon may be loaded from the Instrument (e.g., the surgical microscope system) and then the system may wait for the commands to be provided to the Instrument. The (user-specific) voice profile may be migrated to the instrument before it is used. For example, the voice profile may be created and transferred manually to the Instrument using the Serial Communication Interface. Alternatively, a self-hosted Wireless Local Area Network (e.g., an ad-hoc wireless network) may be used to push the voice profiles from a surgeon's device to the Instrument. To resolve potential security issues of external data injection, a controlled authentication system can be built around the self-hosted device by limiting the types of files used by the application which will be interacting with the microscope.

The commands captured (e.g., recognized) by the system may be mapped against a predefined set of commands (e.g. the plurality of commands associated with the plurality of keywords or key phrases) within the system and may then be validated. Upon successful validation of commands, a text command may be created, which may be fed into the software processing pipeline and the system will be executing the commands.

For example, functionalities like switching many modes between White light and different fluorescence modes, controlling the illumination, zoom, focus, working distance can be done via voice, which may improve the entire work experience of the surgeon. The system may also support many more commands which can be configured using a configuration map (i.e. mapping), and those commands may be available for the user to use.

The proposed concept is proposed to provide offline and "on the edge" voice detection, which may result in faster response times and prevent further security issues due to uncontrolled access of the instrument from outside the knowledge of the user or organization. Thus, various examples of the present disclosure relate to an offline voice-control system, which is based on using a selective voice profile.

Figure 3:
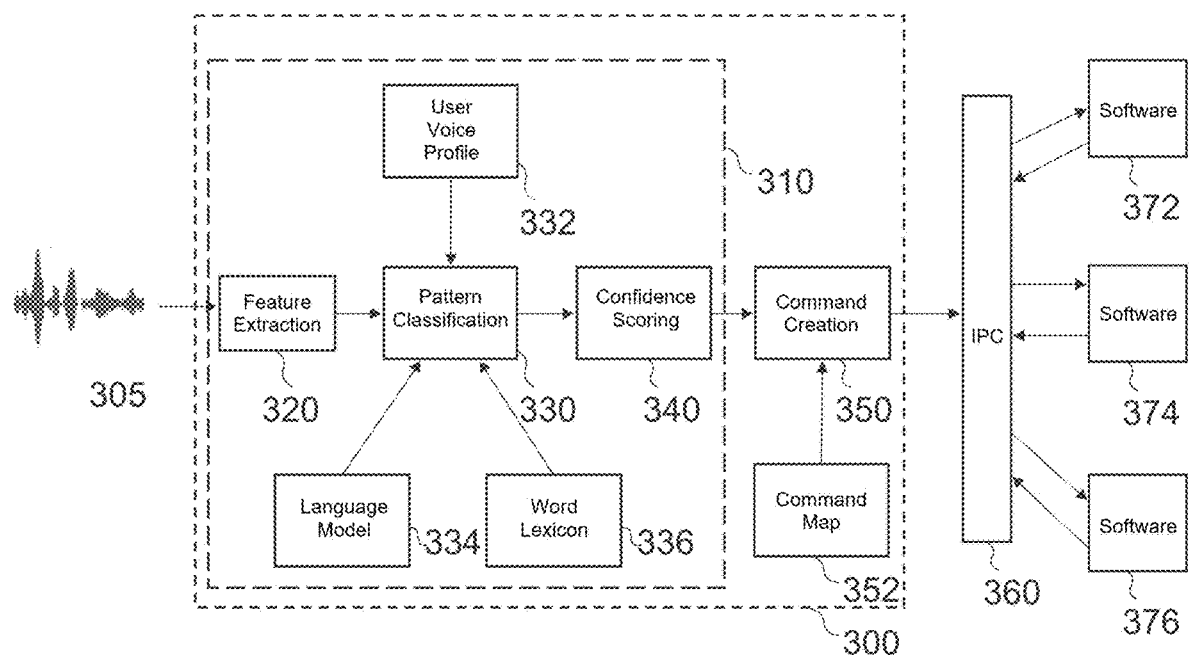
FIG. 3 shows a schematic diagram of an example of a system for speech control of a surgical microscope system.
Figure 4:
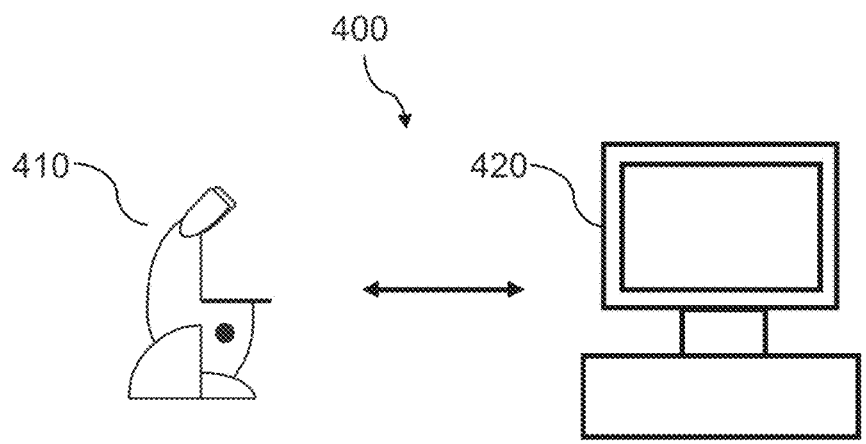
FIG. 4 shows a schematic diagram of an example of a system comprising a microscope and a computer system.

FIG. 3 shows a schematic diagram of an example of a system for speech control of a surgical microscope system. The diagram explains the interactions in the proposed concept. FIG. 3 shows a system/speech manager component 300, which may be implemented by, or correspond to, the system 110 shown in connection with FIGS. 1a to 1b. The system/speech manager component 300 comprises a speech application programming interface (SAPI) 310 with a feature extraction component 320 and a pattern classification component 330, which uses a user voice profile 332, a language model 334 and a word lexicon 336 (which may contain keywords and key phrases), and confidence scoring component 340. The system/speech manager component 300 further comprises a command creation component 350, which uses a command map 352. An input command 305 is inserted, as audio signal, into the system/speech manager component 300, processed by the feature extraction component 320 (to identify feature components of the input signals), subsequently processed by the pattern classification component 330 (based on the user voice profile 332, the language model 334 and the word lexicon 336), e.g., to extract a sequence of words from the input command, subsequently processed by the confidence scoring component 340 (in order to generate a confidence score), and provided to the command creation component 350, which uses the commands map 352 to identify and create the commands. The identified commands are provided to an Inter-Process-Communication (IPC) component 360, which provides the commands to software modules 372; 374; 376. The software modules may perform two-way communication with the IPC component 360.

In the following, use cases are presented, where the proposed concept may be implemented and thus bring a positive impact in the workflow and instrument interaction. However, the proposed concept is not limited to these uses cases.

For examples, the proposed concept may be used for easy controlling of the Instrument by voice, which may yield a better user experience. The settings for peripherals like handle and footswitch assignments may be done, assigned and controlled through voice. Furthermore, a request can be made to initiate recordings and capture images immediately without searching for the assigned button or asking an assistant to initiate those. Mechanism built on the proposed concept can be leveraged to "control" external devices like an endoscope (e.g., to switch the endoscope on or off) and an image-guided surgery (IGS) (e.g., to switch the IGS on or off) with no loss of concentration or heads down time.

More details and aspects of the voice profile-based control of the microscope are mentioned in connection with the proposed concept or one or more examples described above or below (e.g., FIGS. 1a to 2, 4). The profile-based control of the microscope may comprise one or more additional optional features corresponding to one or more aspects of the proposed concept or one or more examples described above or below.

As used herein the term "and/or" includes any and all combinations of one or more of the associated listed items and may be abbreviated as "/".

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus.

Some embodiments relate to a microscope comprising a system as described in connection with one or more of the FIGS. 1 to 3. Alternatively, a microscope may be part of or connected to a system as described in connection with one or more of the FIGS. 1 to 3. FIG. 4 shows a schematic illustration of a system 400 configured to perform a method described herein. The system 400 comprises a microscope 410 and a computer system 420. The microscope 410 is configured to take images and is connected to the computer system 420. The computer system 420 is configured to execute at least a part of a method described herein. The computer system 420 may be configured to execute a machine learning algorithm. The computer system 420 and microscope 410 may be separate entities but can also be integrated together in one common housing. The computer system 420 may be part of a central processing system of the microscope 410 and/or the computer system 420 may be part of a subcomponent of the microscope 410, such as a sensor, an actor, a camera or an illumination unit, etc. of the microscope 410.

The computer system 420 may be a local computer device (e.g., personal computer, laptop, tablet computer or mobile phone) with one or more processors and one or more storage devices or may be a distributed computer system (e.g., a cloud computing system with one or more processors and one or more storage devices distributed at various locations, for example, at a local client and/or one or more remote server farms and/or data centers). The computer system 420 may comprise any circuit or combination of circuits. In one embodiment, the computer system 420 may include one or more processors which can be of any type. As used herein, processor may mean any type of computational circuit, such as but not limited to a microprocessor, a microcontroller, a complex instruction set computing (CISC) microprocessor, a reduced instruction set computing (RISC) microprocessor, a very long instruction word (VLIW) microprocessor, a graphics processor, a digital signal processor (DSP), multiple core processor, a field programmable gate array (FPGA), for example, of a microscope or a microscope component (e.g., camera) or any other type of processor or processing circuit. Other types of circuits that may be included in the computer system 420 may be a custom circuit, an application-specific integrated circuit (ASIC), or the like, such as, for example, one or more circuits (such as a communication circuit) for use in wireless devices like mobile telephones, tablet computers, laptop computers, two-way radios, and similar electronic systems. The computer system 420 may include one or more storage devices, which may include one or more memory elements suitable to the particular application, such as a main memory in the form of random access memory (RAM), one or more hard drives, and/or one or more drives that handle removable media such as compact disks (CD), flash memory cards, digital video disk (DVD), and the like. The computer system 420 may also include a display device, one or more speakers, and a keyboard and/or controller, which can include a mouse, trackball, touch screen, voice-recognition device, or any other device that permits a system user to input information into and receive information from the computer system 420.

Some or all of the method steps may be executed by (or using) a hardware apparatus, like for example, a processor, a microprocessor, a programmable computer or an electronic circuit. In some embodiments, some one or more of the most important method steps may be executed by such an apparatus.

Depending on certain implementation requirements, embodiments of the invention can be implemented in hardware or in software. The implementation can be performed using a nontransitory storage medium such as a digital storage medium, for example a floppy disc, a DVD, a Blu-Ray, a CD, a ROM, a PROM, and EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments according to the invention comprise a data carrier having electronically readable control signals, which are capable of cooperating with a programmable computer system, such that one of the methods described herein is performed.

Generally, embodiments of the present invention can be implemented as a computer program product with a program code, the program code being operative for performing one of the methods when the computer program product runs on a computer. The program code may, for example, be stored on a machine readable carrier.

Other embodiments comprise the computer program for performing one of the methods described herein, stored on a machine readable carrier.

In other words, an embodiment of the present invention is, therefore, a computer program having a program code for performing one of the methods described herein, when the computer program runs on a computer.

A further embodiment of the present invention is, therefore, a storage medium (or a data carrier, or a computer-readable medium) comprising, stored thereon, the computer program for performing one of the methods described herein when it is performed by a processor. The data carrier, the digital storage medium or the recorded medium are typically tangible and/or non-transitionary. A further embodiment of the present invention is an apparatus as described herein comprising a processor and the storage medium.

A further embodiment of the invention is, therefore, a data stream or a sequence of signals representing the computer program for performing one of the methods described herein. The data stream or the sequence of signals may, for example, be configured to be transferred via a data communication connection, for example, via the internet.

A further embodiment comprises a processing means, for example, a computer or a programmable logic device, configured to, or adapted to, perform one of the methods described herein.

A further embodiment comprises a computer having installed thereon the computer program for performing one of the methods described herein.

A further embodiment according to the invention comprises an apparatus or a system configured to transfer (for example, electronically or optically) a computer program for performing one of the methods described herein to a receiver. The receiver may, for example, be a computer, a mobile device, a memory device or the like. The apparatus or system may, for example, comprise a file server for transferring the computer program to the receiver.

In some embodiments, a programmable logic device (for example, a field programmable gate array) may be used to perform some or all of the functionalities of the methods described herein. In some embodiments, a field programmable gate array may cooperate with a microprocessor in order to perform one of the methods described herein. Generally, the methods are preferably performed by any hardware apparatus.

LIST OF REFERENCE SIGNS

100 Surgical microscope system
105 Base unit
110 System
120 Microscope
130 Microphone
140 Arm
150 Handles
160 Display
210 Obtaining an audio signal
220 Analyzing the audio signal
230 Controlling the surgical microscope system
300 system/speech manager component
305 Input command
310 Speech application programming interface
320 Feature extraction component
330 Patten classification component
332 User voice profile
334 language model
336 Word lexicon
340 Confidence scoring component
350 Command creation component
352 Command map
360 Inter-Process-Communication component
372, 374, 376 Software modules
400 System
410 Microscope
420 Computer system
112 Interface(s)
114 Processor(s)
116 Storage Device(s)

The invention claimed is:

1. A system for a surgical microscope system, the system comprising one or more processors and one or more storage devices, wherein the system is configured to:
   obtain an audio signal from a microphone of the surgical microscope system;
   analyze the audio signal locally to detect one or more spoken commands within the audio signal, wherein a user-specific voice profile is used to determine whether the one or more spoken commands are uttered by a user associated with the user-specific voice profile;
   determine a confidence level for the detection of the one or more spoken commands, the confidence level indicating a likelihood for words in the one or more spoken commands being recognized correctly and for the one or more spoken commands being uttered by the user associated with the user-specific voice profile; and
   control the surgical microscope system when the confidence level is sufficiently high based on the detected one or more spoken commands if the one or more spoken commands are uttered by the user associated with the user-specific voice profile.

2. The system according to claim 1, wherein the system is configured to discard spoken commands of users other than the user associated with the user-specific voice profile.

3. The system according to claim 1, wherein the user-specific voice profile is specific to a surgeon actively using the surgical microscope system and/or to a surgeon that is in command of the surgical microscope system.

4. The system according to claim 1, wherein the system is configured to load the user-specific voice profile from the one or more storage devices based on a sign-in of the user at the surgical microscope system.

5. The system according to claim 4, wherein a single user-specific voice profile is loaded for a single user of the surgical microscope system.

6. The system according to claim 1, wherein two or more user-specific voice profiles are used to determine whether the one or more spoken commands are uttered by a user of two or more users associated with two or more user-specific voice profiles, with each user being associated with one of the voice profiles, wherein the system is configured to identify the user of the two or more users using the voice profile associated with the user, and to control the surgical microscope system based on the detected one or more spoken commands if the user that has uttered the one or more spoken commands is a surgeon actively using the surgical microscope system.

7. The system according to claim 1, wherein the user-specific voice profile is based on at least one of a wavelength range of the voice of the user and a vocal amplitude of the user.

8. The system according to claim 1, wherein the system is configured to analyze the audio signal locally to detect one or more keywords or key phrases, and to detect the one or more spoken commands based on an association between the one or more keywords or key phrases and the one or more spoken commands.

9. The system according to claim 1, wherein the system is configured to detect the one or more spoken commands within the audio signal without involving an external entity.

10. The system according to claim 1, wherein the system is configured to analyze the audio signal using the user-specific voice profile, using a language model and using a dictionary of keywords or key phrases.

11. The system according to claim 10, wherein the dictionary of keywords or key phrases comprises keywords or key phrases that are associated with a plurality of commands available at the microscope system, wherein the system comprises a mapping between the keywords or key phrases and the plurality of commands, and wherein the system is configured to control the surgical microscope system based on the mapping between the keywords or key phrases and the plurality of commands.

12. The system according to claim 1, wherein the system is configured to control at least one of an illumination of the surgical microscope system, an imaging mode of a microscope of the surgical microscope system, a zoom functionality of the microscope, a focusing functionality of the microscope, an auto-focusing functionality of the microscope, a robotic arm of the surgical microscope system, a video recording functionality of the surgical microscope system, and a still image recording functionality of the surgical microscope system.

13. A surgical microscope system comprising the system according to claim 1, a microscope, and a microphone.

14. A method for a surgical microscope system, the method comprising:
   obtaining an audio signal from a microphone of the surgical microscope system;
   analyzing the audio signal locally to detect one or more spoken commands within the audio signal, wherein a user-specific voice profile is used to determine whether the one or more spoken commands are uttered by a user associated with the user-specific voice profile;
   determining a confidence level for the detection of the one or more spoken commands, the confidence level indicating a likelihood for words in the one or more spoken commands being recognized correctly and for the one or more spoken commands being uttered by the user associated with the user-specific voice profile; and controlling the surgical microscope system when the confidence level is sufficiently high based on the detected one or more spoken commands if the one or more spoken commands are uttered by the user associated with the user-specific voice profile.

15. A non-transitory, computer-readable medium comprising a program code that, when the program code is executed on a processor, a computer, or a programmable hardware component, causes the processor, computer, or programmable hardware component to perform the method of claim 14.

\* \* \* \* \*